US008866896B2

(12) United States Patent
Hatakeyama

(10) Patent No.: US 8,866,896 B2
(45) Date of Patent: Oct. 21, 2014

(54) BIOLOGICAL BODY STATE ASSESSMENT DEVICE INCLUDING DROWSINESS OCCURRENCE ASSESSMENT

(75) Inventor: Yoshiyuki Hatakeyama, Toyota (JP)

(73) Assignee: Toyota Jidosha Kabushiki Kaisha, Aichi-ken (JP)

(*) Notice: Subject to any disclaimer, the term of this patent is extended or adjusted under 35 U.S.C. 154(b) by 142 days.

(21) Appl. No.: 13/639,208

(22) PCT Filed: Apr. 5, 2010

(86) PCT No.: PCT/JP2010/056177
§ 371 (c)(1),
(2), (4) Date: Oct. 4, 2012

(87) PCT Pub. No.: WO2011/125166
PCT Pub. Date: Oct. 13, 2011

(65) Prior Publication Data
US 2013/0021463 A1 Jan. 24, 2013

(51) Int. Cl.
H04N 7/18 (2006.01)
A61B 5/00 (2006.01)
G06K 9/00 (2006.01)
A61B 5/11 (2006.01)
A61B 5/18 (2006.01)
G08B 21/06 (2006.01)
G02B 27/01 (2006.01)
B60K 28/06 (2006.01)

(52) U.S. Cl.
CPC . A61B 5/18 (2013.01); A61B 5/746 (2013.01); G02B 2027/0187 (2013.01); G02B 2027/0138 (2013.01); G06K 9/00845 (2013.01); A61B 5/7275 (2013.01); A61B 5/11 (2013.01); B60K 28/066 (2013.01); G02B 27/017 (2013.01); A61B 5/1128 (2013.01); G08B 21/06 (2013.01); A61B 5/1103 (2013.01)
USPC .......................................................... 348/78

(58) Field of Classification Search
CPC .................................. A61B 3/113; A61B 5/18
USPC ........................................................... 348/78
See application file for complete search history.

(56) References Cited

U.S. PATENT DOCUMENTS 5,689,241 A * 11/1997 Clarke et al. ................... 340/575
6,927,694 B1 8/2005 Smith et al.
(Continued)

FOREIGN PATENT DOCUMENTS

JP 7-241283 A 9/1995
JP 8-290726 A 11/1996
(Continued)

OTHER PUBLICATIONS

Marco Javier Flores et al, "Real-Time Warning System for Driver Drowsiness Detection Using Visual Information", Journal of Intelligent and Robotic Systems ; Theory and Applications—(Incorporating Mechatronic Systems Engineering), Kluwer Academic Publishers, DO, vol. 59, No. 2, Dec. 5, 2009, p. 103-p. 125, XP019821342.
(Continued)

Primary Examiner — Sath V Perungavoor
Assistant Examiner — James Pontius
(74) Attorney, Agent, or Firm — Sughrue Mion, PLLC

(57) ABSTRACT

Disclosed is a biological body state assessment device capable of accurately assessing an absentminded state of a driver. The biological body state assessment device first acquires face image data of a face image capturing camera, detects an eye open time and a face direction left/right angle of a driver from face image data, calculates variation in the eye open time of the driver and variation in the face direction left/right angle of the driver, and performs threshold processing on the variation in the eye open time and the variation in the face direction left/right angle to detect the absentminded state of the driver. The biological body state assessment device assesses the possibility of the occurrence of drowsiness of the driver in the future using a line fitting method on the basis of an absentminded detection flag and the variation in the eye open time, and when it is assessed that there is the possibility of the occurrence of drowsiness, estimates an expected drowsiness occurrence time of the driver.

6 Claims, 13 Drawing Sheets

(56) References Cited

U.S. PATENT DOCUMENTS

| | | |
|---|---|---|
| 2002/0181774 A1 | 12/2002 | Ishikura |
| 2009/0268022 A1 | 10/2009 | Omi |
| 2010/0214105 A1* | 8/2010 | Manotas, Jr. .................. 340/575 |
| 2011/0313259 A1 | 12/2011 | Hatakeyama et al. |

FOREIGN PATENT DOCUMENTS

| | | |
|---|---|---|
| JP | 9-254742 A | 9/1997 |
| JP | 10-272959 A | 10/1998 |
| JP | 2002-352229 A | 12/2002 |
| JP | 2003-571 A | 1/2003 |
| JP | 2004-041485 A | 2/2004 |
| JP | 2006-151287 A | 6/2006 |
| JP | 2007-265377 A | 10/2007 |
| JP | 2008-204185 A | 9/2008 |
| JP | 2009-261516 A | 11/2009 |
| JP | 2010-68848 A | 4/2010 |
| WO | 2008/044119 A2 | 4/2008 |
| WO | 2010092860 A1 | 8/2010 |

OTHER PUBLICATIONS

Marco Javier Flores et al, "Real-time drowsiness detection system for an intelligent vehicle", Intelligent Vehicles Symposium, 2008 IEEE, IEEE, Piscataway, NJ, USA, Jun. 4, 2008, p. 637-p. 642, XP031318770.

Jorge Batista, "A Drowsiness and Point of Attention Monitoring System for Driver Vigilance", Intelligent Transportation Systems Conference, 2007. ITSC 2007. IEEE, IEEE, PI, Sep. 1, 2007, p. 702-p. 708, XP031151447.

* cited by examiner

*Fig.4*

| START TIME | END TIME | EYE OPEN TIME |
|---|---|---|
| $ts_1$ | $te_1$ | $to_1$ |
| $ts_2$ | $te_2$ | $to_2$ |
| $ts_3$ | $te_3$ | $to_3$ |
| ⋮ | ⋮ | ⋮ |
| $ts_{n-2}$ | $te_{n-2}$ | $to_{n-2}$ |
| $ts_{n-1}$ | $te_{n-1}$ | $to_{n-1}$ |
| $ts_n$ | $te_n$ | $to_n$ |

Fig.6

| TRAVELING TIME t | FACE DIRECTION LEFT/RIGHT ANGLE $\beta$ |
|---|---|
| $t_1$ | $\beta_1$ |
| $t_2$ | $\beta_2$ |
| ⋮ | ⋮ |
| $t_{n-2}$ | $\beta_{n-2}$ |
| $t_{n-1}$ | $\beta_{n-1}$ |
| $t_n$ | $\beta_n$ | n:NUMBER OF PIECES OF DATA (A)

(B)

BIOLOGICAL BODY STATE ASSESSMENT DEVICE INCLUDING DROWSINESS OCCURRENCE ASSESSMENT

CROSS REFERENCE TO RELATED APPLICATIONS

This application is a National Stage of International Application No. PCT/JP2010/056177 filed Apr. 5, 2010, the contents of all of which are incorporated herein by reference in their entirety.

TECHNICAL FIELD

The present invention relates to a biological body state assessment device which assesses a biological body state of a driver.

BACKGROUND ART

As a biological body state assessment device of the related art, a biological body state assessment device described in Patent Literature 1 is known. The biological body state assessment device described in Patent Literature 1 detects driver information, such as an eye closure time ratio reflecting vigilance, and driver information, such as a head vibration transmission rate reflecting the degree of attention concentration, calculates the average value and standard deviation of an individual driver of each piece of driver information, and assesses the drowsy state, the drowsiness-conflicting state, the concentration state, and the carelessness state of the driver on the basis of the average value, the standard deviation, and vehicle/driving environment information.

CITATION LIST

Patent Literature

[Patent Literature 1] Japanese Unexamined Patent Application Publication No. 2007-265377

SUMMARY OF INVENTION

Technical Problem

However, in the technique of the related art, since there is no index (feature quantity) having different values between an absentminded state before drowsiness occurs and other states, it is difficult to definitively assess an unclear biological body state, such as an absentminded state.

An object of the invention is to provide a biological body state assessment device capable of accurately assessing an absentminded state of a driver.

Solution to Problem

A biological body state assessment device of the invention includes face information acquisition means for acquiring face information of a driver, eye open time variation calculation means for calculating variation in the eye open time of the driver on the basis of the face information of the driver, face direction variation calculation means for calculating variation in the face direction of the driver on the basis of the face information of the driver, and vigilance assessment means for assessing the vigilance of the driver on the basis of the variation in the eye open time of the driver and the variation in the face direction of the driver.

In the biological body state assessment device of the invention, the variation in the eye open time of the driver and the variation in the face direction of the driver are calculated on the basis of the face information of the driver. If the variation in the eye open time of the driver increases and the variation in the face direction of the driver decreases, the vigilance of the driver is lowered, and the driver tends to transit to an absentminded state. Therefore, it is possible to assess the vigilance of the driver on the basis of the variation in the eye open time of the driver and the variation in the face direction of the driver, thereby increasing the assessment accuracy of the absentminded state.

It is preferable that the vigilance assessment means assesses that, as the variation in the face direction of the driver becomes small, the vigilance of the driver is lowered. Therefore, if the variation in the face direction of the driver becomes small, it is possible to assess that the driver tends to be in the absentminded state.

It is preferable that the biological body state assessment device further includes drowsiness occurrence assessment means for assessing whether or not there is the possibility of the occurrence of drowsiness in the driver on the basis of the increase/decrease tendency of the variation in the eye open time of the driver after the absentminded state of the driver has been detected from the vigilance of the driver assessed by the vigilance assessment means. When the variation in the eye open time of the driver tends to decrease, the driver transits from the absentminded state to the drowsy state. In this way, it is assessed whether or not there is the possibility of the occurrence of drowsiness in the driver, thereby giving the driver a countermeasure for suppressing drowsiness.

At this time, it is preferable that the biological body state assessment device further includes drowsiness occurrence time prediction means for predicting the time at which drowsiness occurs in the driver on the basis of a slope of an approximate expression obtained by approximating the variation in the eye open time of the driver and a threshold value set in advance when the drowsiness occurrence assessment means assesses that there is the possibility of the occurrence of drowsiness in the driver. In this case, for example, the time at which drowsiness occurs or the time until drowsiness occurs is notified to the driver, thereby recommending the driver to get rest.

Advantageous Effects of Invention

According to the invention, it is possible to accurately assess the absentminded state of the driver. Therefore, it becomes possible to discriminate the biological body state of the driver in more detail.

BRIEF DESCRIPTION OF DRAWINGS

FIG. 4 is a table showing an example of an eye open time storage buffer.

FIG. 6 is a table showing an example of a face direction angle storage buffer.

DESCRIPTION OF EMBODIMENTS

Hereinafter, a preferred embodiment of a biological body state assessment device according to the invention will be described in detail with reference to the drawings.

Figure 1:
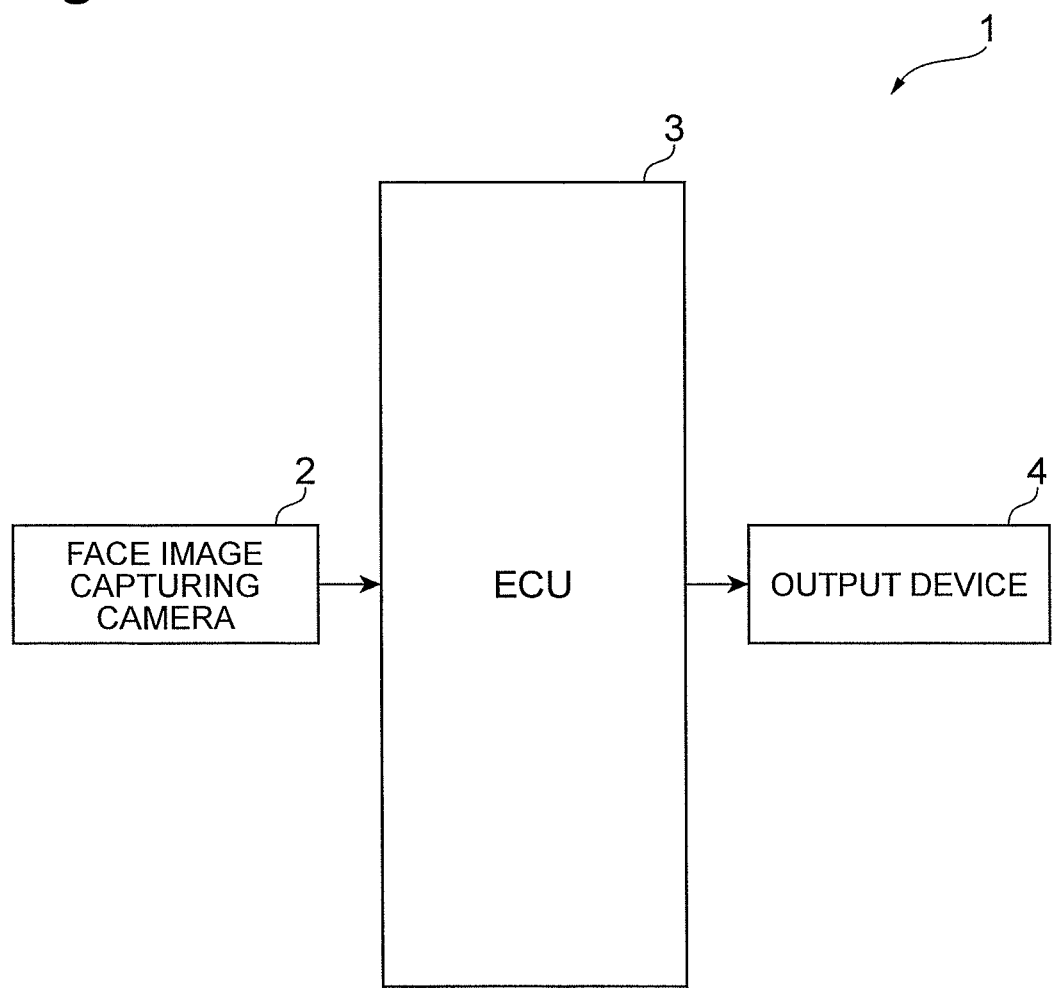
FIG. 1 is a block diagram showing the schematic configuration of an embodiment of a biological body state assessment device according to the invention.

FIG. 1 is a block diagram showing the schematic configuration of an embodiment of a biological body state assessment device according to the invention. A biological body state assessment device 1 of this embodiment is a device which is mounted in a vehicle to assess the biological body state of the driver of the vehicle.

The biological body state assessment device 1 includes a face image capturing camera 2, an ECU (Electronic Control Unit) 3, and an output device 4. The face image capturing camera 2 images the face of the driver to generate a face image. As the output unit 4, a device which generates a sound output, or a device which performs screen display is used.

The ECU 3 has a CPU, a memory, such as a ROM or a RAM, an input/output circuit, and the like. The ECU 3 inputs the image captured by the face image capturing camera 2, performs predetermined processing, assesses the vigilance of the driver, discriminates the biological body state (vigilance state, absentminded state, drowsy state, or the like) of the driver from the vigilance, and sends the discrimination result to the output device 4.

Figure 2:
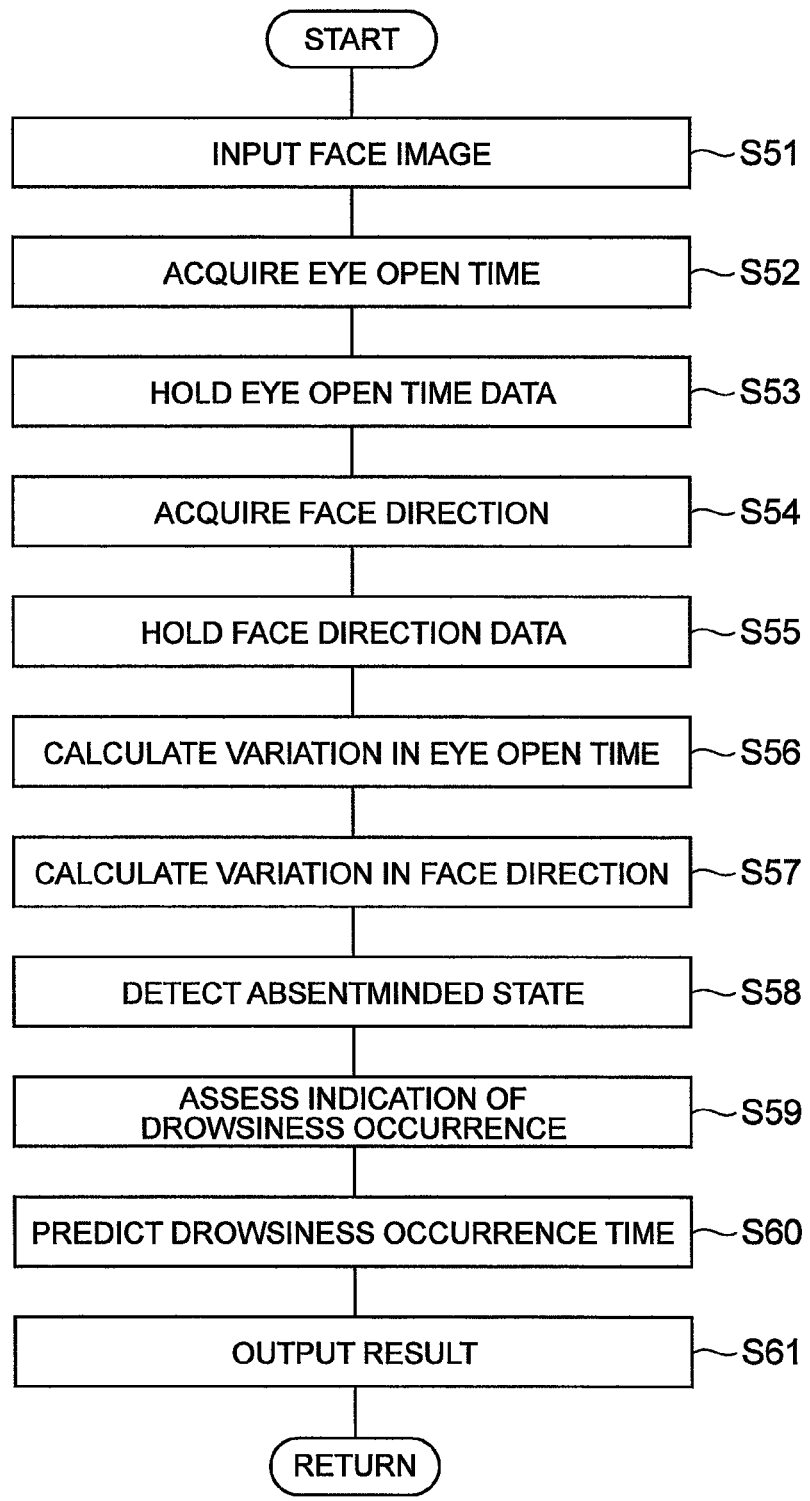
FIG. 2 is a flowchart showing a processing procedure which is executed by an ECU shown in FIG. 1.
Figure 3:
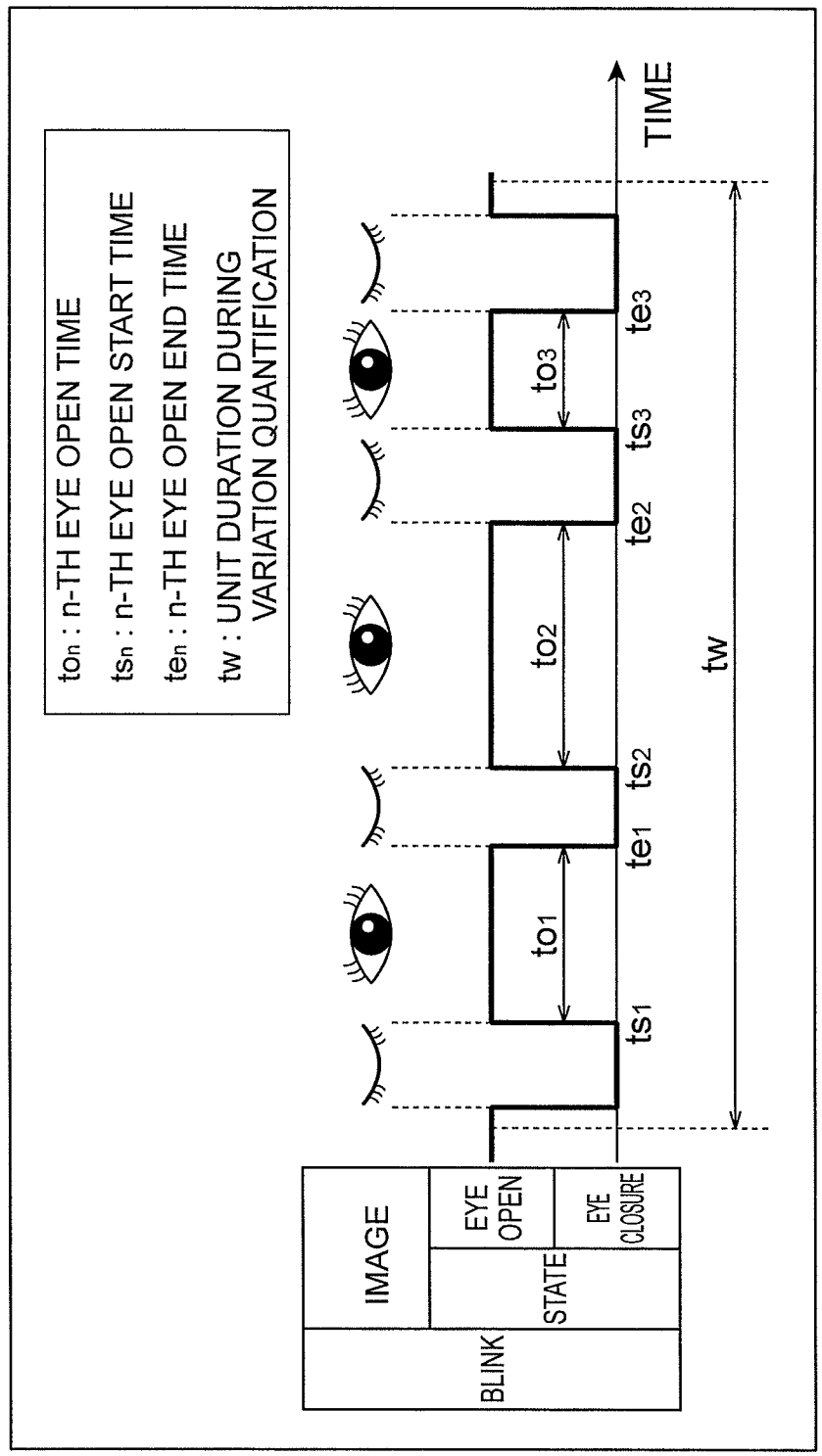
FIG. 3 is a diagram showing an example of variation in an eye open time within a unit duration.

FIG. 2 is a flowchart showing a processing procedure which is executed by an ECU 3. In FIG. 2, first, face image data of the face image capturing camera 2 is acquired (Step S51). As shown in FIG. 3, the opening/closing of the eyelids is assessed from the face image data, and the time (eye open time) for which the eyes are open is detected (Step S52). In FIG. 3, $to_n$ denotes an n-th eye open time, $ts_n$ denotes an n-th eye open start time, and $te_n$ denotes an n-th eye open end time.

Next, as shown in FIG. 4, eye open time data (start time $ts_n$, end time $te_n$, eye open time $to_n$) is held in an eye open time storage buffer (Step S53). The size of the eye open time storage buffer is set so as to satisfy $te_n - ts_1 > tw$. Note that tw (see FIG. 3) is a unit duration during quantification of variation (described below) in the eye open time.

Figure 5:
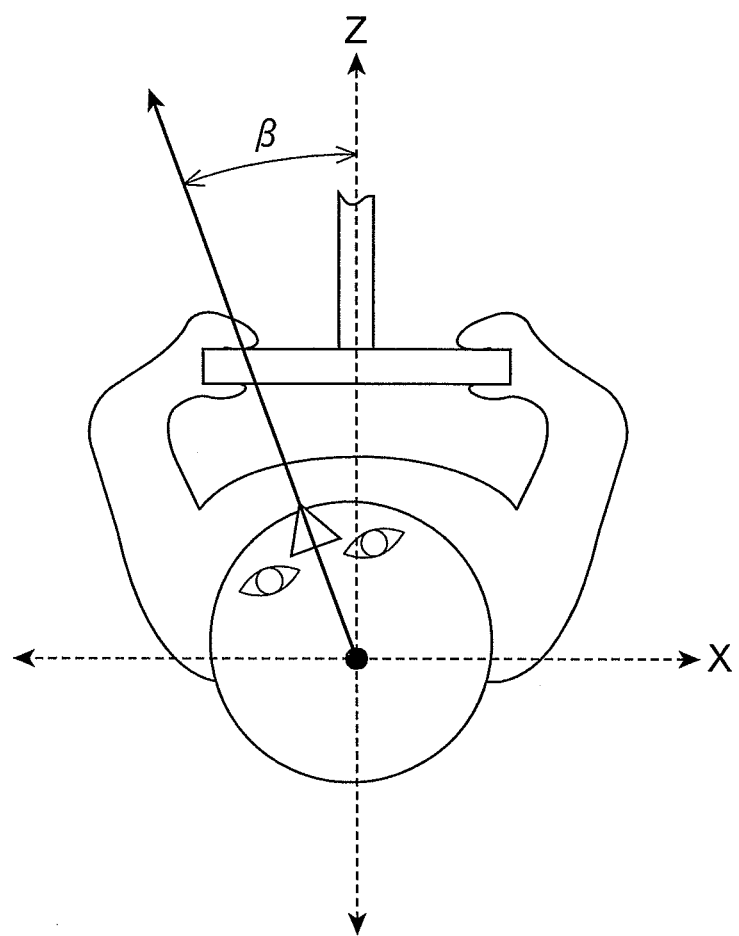
FIG. 5 is a conceptual diagram showing a face direction left/right angle of a driver.

Next, as shown in FIG. 5, the face direction left/right angle β of the driver is detected from face image data acquired in Step S51 (Step S54). The face direction left/right angle β is the face direction angle with respect to the vehicle front-back direction (Z-axis direction), and in this case, the right direction is positive.

Next, as shown in FIG. 6, face direction left/right angle data (traveling time $t_n$, face direction left/right angle ($β_n$)) is held in a face direction angle storage buffer (Step S55). The size of the face direction angle storage buffer is set so as to satisfy $t_n - t_1 > tw$. Note that tw is a unit duration during quantification of variation (described below) in the face direction left/right angle.

Next, a plurality of variations in the eye open time are calculated as a statistical amount (Step S56). The statistical amount is a standard deviation, a dispersion, and the like, and in this case, a standard deviation is calculated. At this time, eye open time data within the unit duration tw is acquired, and the eye open time variation (standard deviation) Tsd is calculated as follows.

eye open time within unit duration $tw = \{to_1, to_2, to_3, \ldots to_n\}$ $$\text{eye open time variation (standard deviation) } Tsd = \sqrt{\frac{1}{n-1}\sum_{i=1}^{n}(to_i - \overline{to})^2} \quad \text{[Equation 1]}$$

n: total number of extracted eye open times
i: eye open time number
$to_i$: i-th eye open time data
$\overline{to}$: average value of n pieces of eye open time data An arbitrary number of pieces of eye open time data previously detected may be acquired to calculate the eye open time variation Tsd. Specifically, an arbitrary number of pieces of eye open time data stored in the eye open time storage buffer shown in FIG. 4 are extracted backward from the latest one. For example, if the latest eye open time is $to_n$, and the number of pieces of eye open time data is 3, the eye open times to be extracted are three of $to_{n-2}$, $to_{n-1}$, and $to_n$. The eye open time variation Tsd is calculated using these pieces of eye open time data by the above-described expression.

Figure 7:
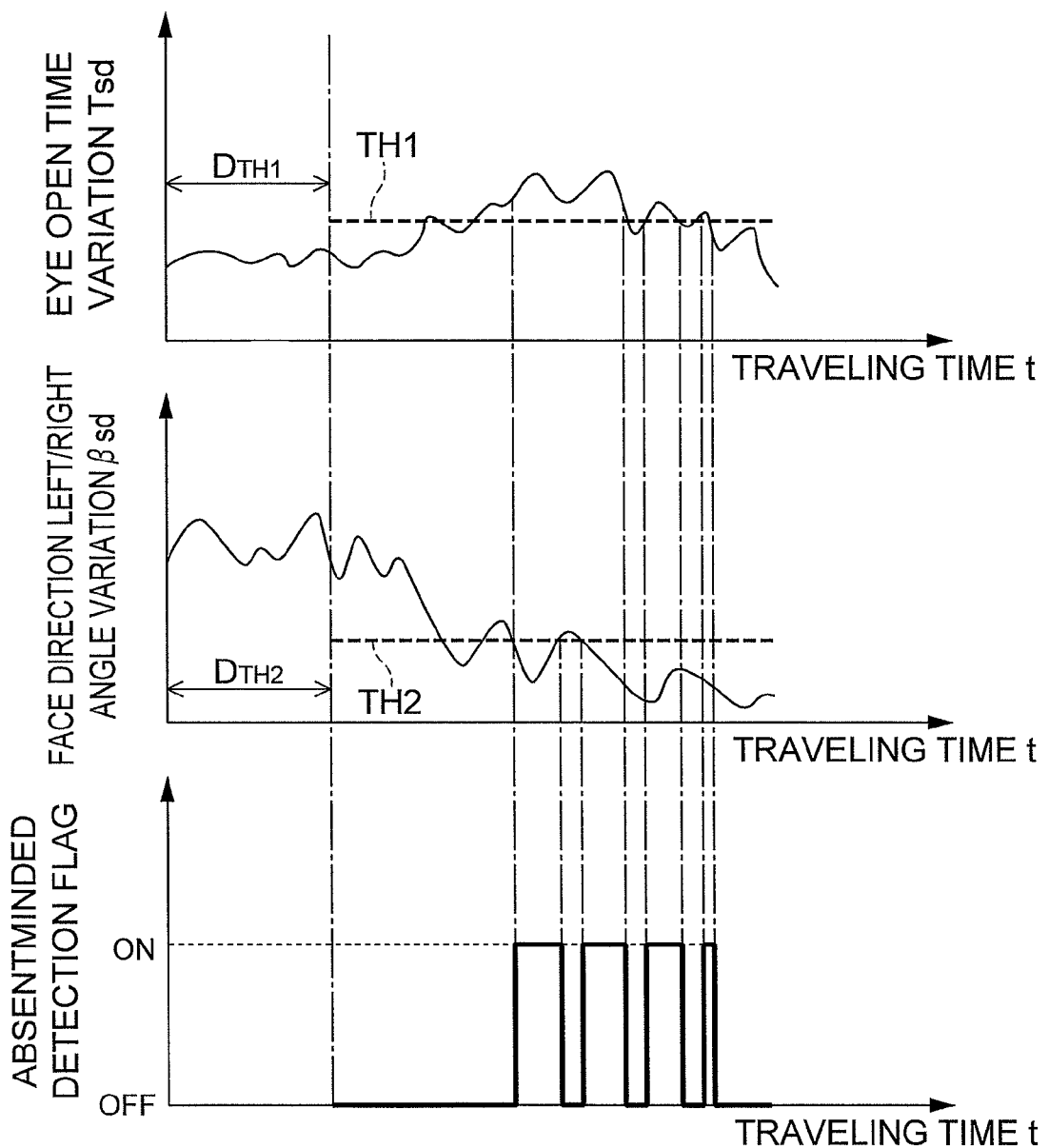
FIG. 7 is a graph showing the relationship between an eye open time variation and a face direction left/right angle variation, and an absentminded detection flag.

Next, variation in a plurality of face direction left/right angles (absolute value) is calculated as a statistical amount (Step S57). The statistical amount is a standard deviation, a dispersion, or the like, and in this case, a standard deviation is calculated. At this time, face direction left/right angle (absolute value) data within the unit duration tw is acquired, and the face direction left/right angle variation (standard deviation) βsd is calculated as follows.

face direction left/right angle (absolute value) within unit duration $tw = \{β_1, β_2, β_3, \ldots β_n\}$ $$\text{face direction left/right variation (standard deviation) } βsd = \sqrt{\frac{1}{n-1}\sum_{i=1}^{n}(β_i - \overline{β})^2} \quad \text{[Equation 2]}$$

n: total number of extracted face direction left/right angles (absolute value)
i: face direction left/right angle (absolute value) data number
$β_i$: i-th face direction left/right angle (absolute value)
$\overline{β}$: average value of n pieces of face direction left/right angle (absolute value) data Next, as shown in FIG. 7, threshold processing is performed on the eye open time variation Tsd and the face direction left/right angle variation βsd, thereby detecting the absentminded state of the driver (Step S58). Specifically, the eye open time variation Tsd is compared with a threshold value TH1, and the face direction left/right angle variation βsd is compared with a threshold value TH2. At this time, when the eye open time variation Tsd(t) and the face direction left/right angle variation βsd(t) at the time t satisfy the following conditions, the absentminded detection flag is ON. When the following conditions are not satisfied, the absentminded detection flag is OFF.

Tsd(t)>TH1
βsd(t)<TH2

In FIG. 7, a section $D_{TH1}$ is a data acquisition section for setting the threshold value TH1, and a section $D_{TH2}$ is a data acquisition section for setting the threshold value TH2.

As a method of setting the threshold value TH1, the following method is used. That is, as the following expression, the threshold value TH1 is set from the statistical amount of the eye open time variation from the start of driving to an arbitrary time $t_n$.

$$TH1 = T\_MEAN\_SD + N \times T\_STDEV\_SD \quad (A)$$

T_MEAN_SD: average value of eye open time variation from start of driving to arbitrary time $t_n$
N: coefficient (for example, 3)
T_STDEV_SD: standard deviation of eye open time variation from start of driving to arbitrary time $t_n$ The name of the driver may be stored in association with the threshold value TH1 as a database, personal authentication may be performed at the time of the start of driving, and the threshold value TH1 may be set with reference to a database corresponding to the driver. In this case, for example, it is necessary that data when the driver uses the device for the first time is held as the threshold value TH1.

The value of the coefficient N in Expression (A) may change depending on an article which is put on by the driver. For example, when the driver puts glasses on, even if not absentminded, the eyes tend to get tired easily compared to the naked eyes, and the eye open time variation increases. For this reason, if the coefficient N increases (for example, N=5), erroneous detection is unlikely to occur. In this case, for example, it is assessed whether or not the driver puts the glasses on by the face image capturing camera 2, and when the driver puts the glasses on, the threshold value TH1 is set with reference to a database for the glasses. When the driver does not put the glasses on, the threshold value TH1 is set with reference to a database for no glasses.

As a method of setting the threshold value TH2, the following method is used. That is, from the following expression, the threshold value TH2 is set from the statistical amount of the face direction left/right angle variation from the start of driving to an arbitrary time $t_n$.

$$TH2 = \beta\_MEAN\_SD - N \times \beta\_STDEV\_SD \quad (B)$$

β_MEAN_SD: average value of face direction left/right angle variation from start of driving to arbitrary time $t_n$
N: coefficient (for example, 2)
β_STDEV_SD: standard deviation of face direction left/right angle variation from start of driving to arbitrary time $t_n$ The name of the driver may be stored in association with the threshold value TH2 as a database, personal authentication may be performed at the time of the start of driving, and the threshold value TH2 may be set with reference to a database corresponding to the driver. In this case, for example, it is necessary that data when the driver uses the device for the first time is held as the threshold value TH2.

Figure 8:
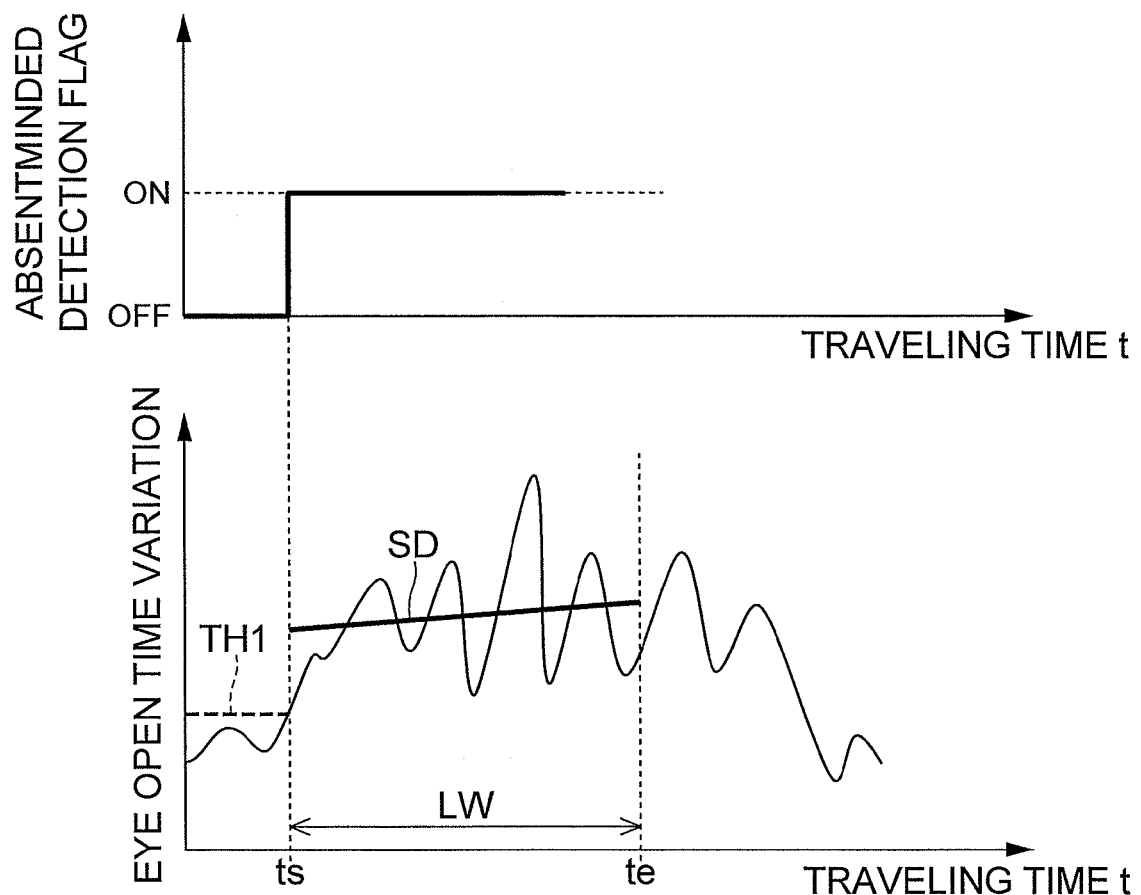
FIG. 8 is a graph showing an example of the relationship between an absentminded detection flag and an eye open time variation.

Next, as shown in FIG. 8, the possibility of the occurrence of drowsiness of the driver in the future is assessed on the basis of the absentminded detection flag and the eye open time variation using a line fitting method (Step S59).

Specifically, the time at which the absentminded detection flag is changed from OFF to ON is set as the leading time $t_s$ of a line fitting section. Next, the time when a line fitting section width LW has elapsed from the time $t_s$ is set as the trailing time $t_e$ of the line fitting section. Next, a line approximate expression is acquired for eye open time variation data of the section of the time $t_s$ to the time $t_e$. As an example of an approximation method, a least-squares method is used. A line approximate expression SD is as follows.

$$SD = At + B \quad (C)$$

The following assessment is performed for the slope A of Expression (C).

A<0 (condition 1)
A≥0 (condition 2)

When A<0 (condition 1) is satisfied, it is estimated that the driver transits from the absentminded state to the drowsy state. When A>0 is satisfied, it is estimated that the driver transits from the absentminded state to the vigilance state.

The line fitting section width LW is set to, for example, three minutes. The reason is that even a short sleep latency (the time until the person falls asleep) of a person (a patient who has a sleep disorder) is at the shortest about three minutes. Accordingly, it is possible to quickly assess the possibility of the occurrence of drowsiness for any driver including a healthy person. The time $t_e$ is the time at which eye open time variation data has been acquired, and is thus the time at which the possibility of the occurrence of drowsiness is assessed.

Figure 9:
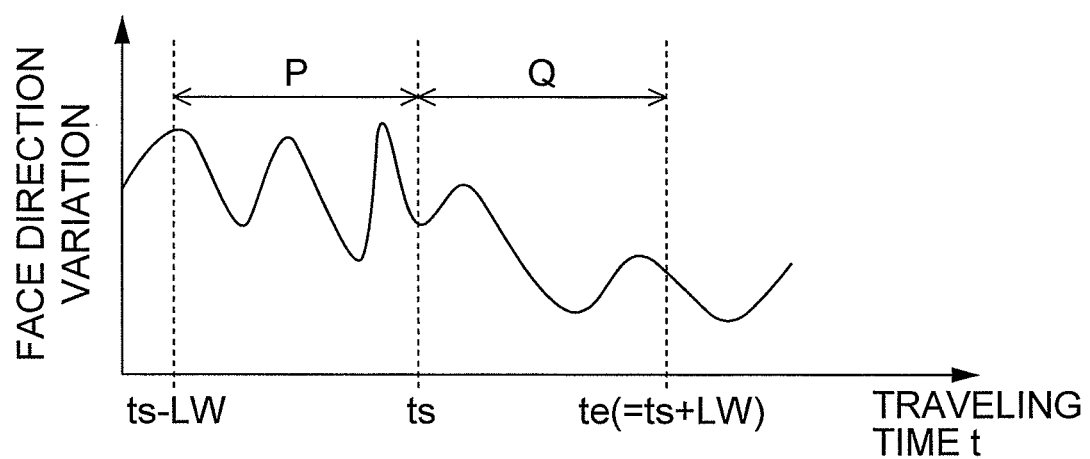
FIG. 9 is a graph showing an example of a face direction left/right angle variation in which two data processing sections are set.

In Expression (C), when it is assessed that A<0 (condition 1) is satisfied, as shown in FIG. 9, two data processing sections P and Q are set for face direction left/right angle variation data. The data processing section P is the duration section from the time ($t_s$−LW) to the time $t_s$, and the data processing section Q is the duration section from the time $t_s$ to the time $t_e$.

Figure 10:
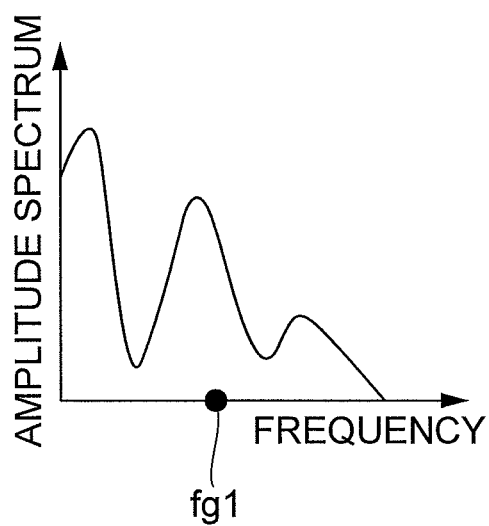
FIG. 10 is a graph showing the frequency distribution of a face direction left/right angle variation in each data processing section shown in FIG. 9.
Figure 10:
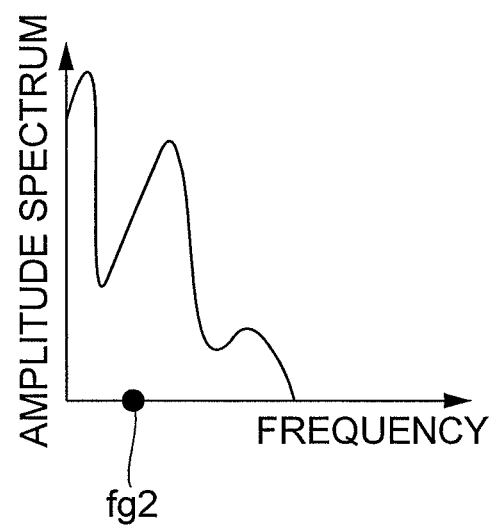

Next, face direction left/right angle variation data of the data processing section P is cut, frequency analysis processing (for example, FFT processing) is performed on face direction left/right angle variation data, and as shown in FIG. 10(A), an amplitude spectrum (frequency distribution) for a frequency component is obtained. A center frequency $fg_1$ in the frequency distribution of face direction left/right angle variation data of the data processing section P is extracted.

In the same manner as described above, face direction left/right angle variation data of the data processing section Q is cut, frequency analysis processing is performed on face direction left/right angle variation data, and a frequency distribution shown in FIG. 10(B) is obtained. A center frequency $fg_2$ in the frequency distribution of face direction left/right angle variation data of the data processing section Q is extracted.

When the relationship between the center frequencies $fg_1$ and $fg_2$ satisfy the following expression, it is assessed that there is the possibility of the occurrence of drowsiness in the driver.

$fg_1 > fg_2$

Figure 11:
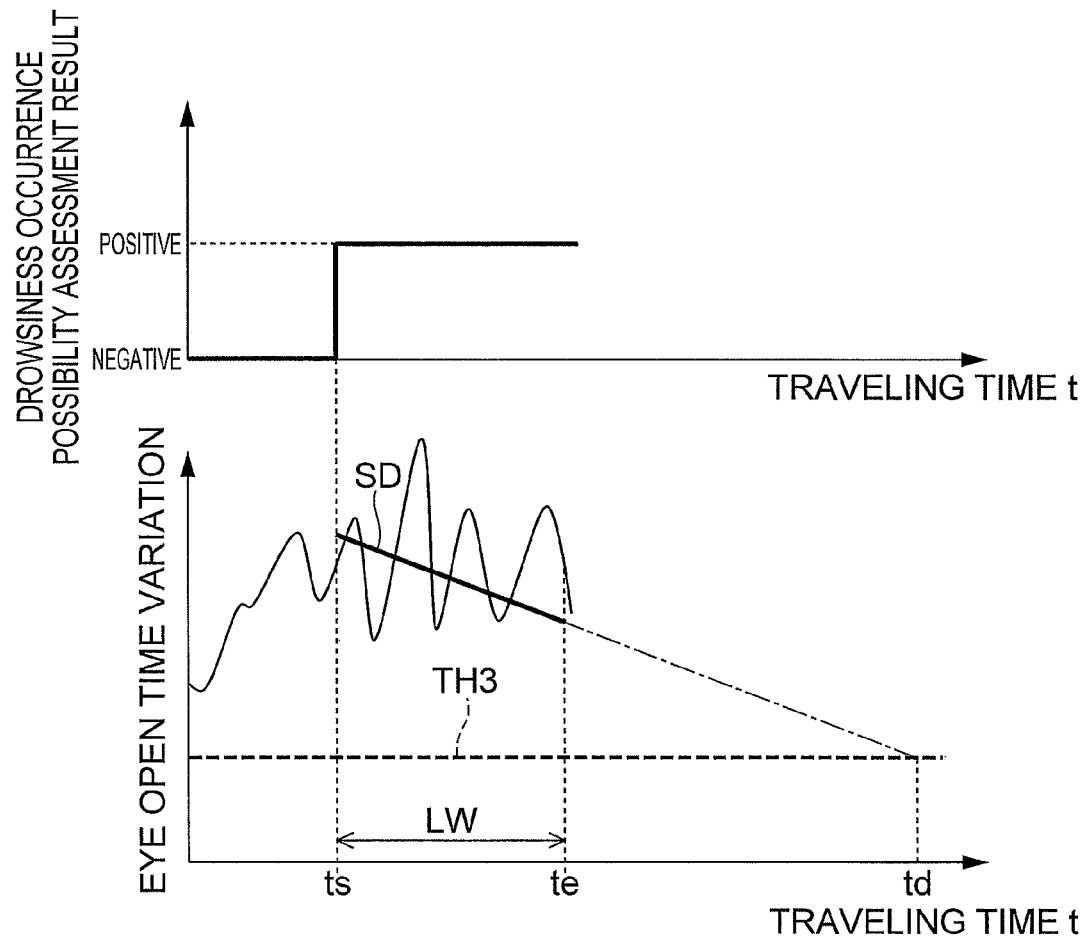
FIG. 11 is a graph showing an example of the relationship between a drowsiness occurrence possibility assessment result and an eye open time variation.

Next, when it is assessed in Step S59 that there is the possibility of the occurrence of drowsiness in the driver, as shown in FIG. 11, an expected drowsiness occurrence time of the driver in the future is estimated using the drowsiness occurrence possibility assessment result and the line approximate expression SD (Step S60). Specifically, first, the time $t_d$ corresponding to an intersection point of a line (expected drowsiness occurrence line) extended from the line approximate expression SD and a threshold value TH3 for drowsiness occurrence state detection is calculated. The time $t_d$ is estimated as an expected drowsiness occurrence time. Since the time $t_e$ becomes the time at which processing for estimating the expected drowsiness occurrence time is performed, the time difference (the required time up to the expected drowsiness occurrence time) between the time $t_d$ and the time $t_e$ is calculated.

Next, as the processing results of Steps S58 to S60, whether or not the driver is in the absentminded state, whether or not there is the possibility of the occurrence of drowsiness in the driver, the required time until drowsiness occurs in the driver, and the like are sent to the output device 4 and then to the driver (Step S61).

Figure 12:
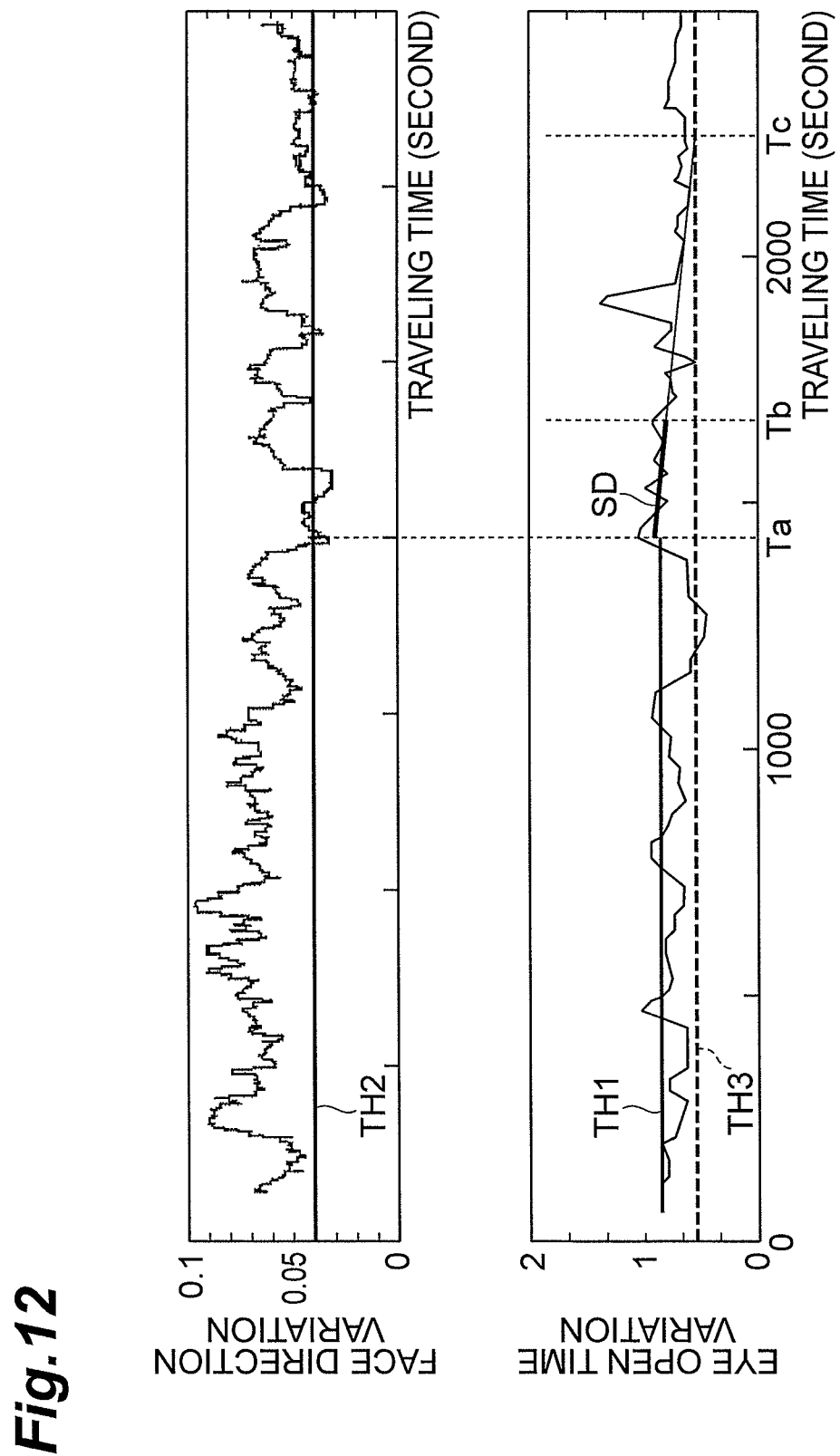
FIG. 12 is a graph showing the relationship between an eye open time variation and a face direction left/right angle variation in an example in which an embodiment of a biological body state assessment device according to the invention is applied to actual traveling.

FIG. 12 shows an example in which the biological body state assessment device 1 is applied to actual traveling. In FIG. 12, the absentminded state of the driver is detected at the time Ta at which the eye open time variation is greater than the threshold value TH1, and the face direction left/right angle variation is smaller than the threshold value TH2. It is expected that the time Tc corresponding to an intersection point of the expected drowsiness occurrence line extended from the line approximate expression SD and the threshold value TH3 is the time at which the driver becomes drowsy. At this time, an actual drowsiness occurrence time declared by the driver is substantially consistent with the time Tc.

Figure 13:
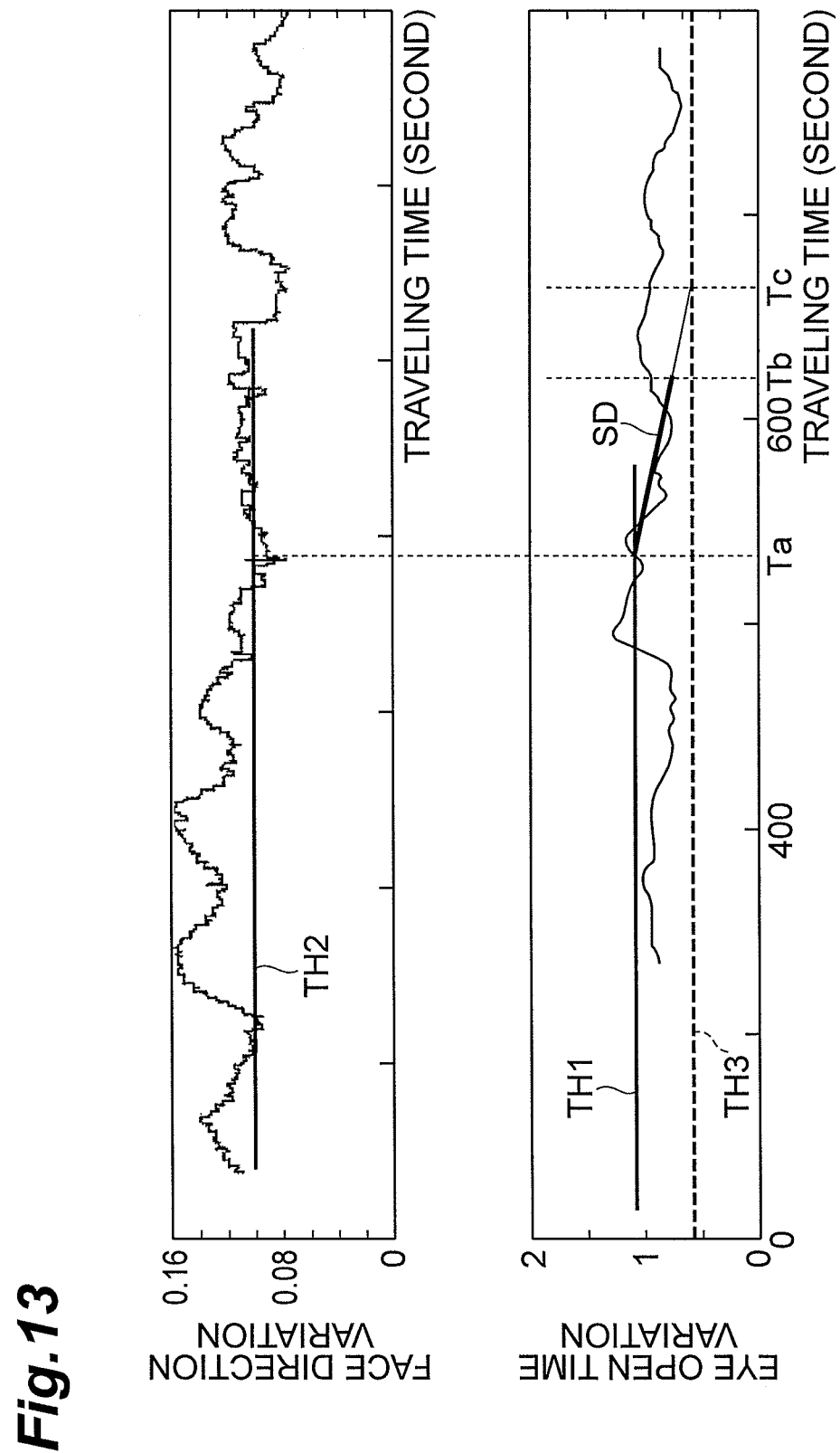
FIG. 13 is a graph showing the relationship between an eye open time variation and a face direction left/right angle variation in another example in which an embodiment of a biological body state assessment device according to the invention is applied to actual traveling.

FIG. 13 shows another example in which the biological body state assessment device 1 is applied to actual traveling. In FIG. 13, the absentminded state of the driver is detected at the time Ta at which the eye open time variation is greater than the threshold value TH1, and the face direction left/right angle variation is smaller than the threshold value TH2. It is expected that the time Tc corresponding to an intersection point of the expected drowsiness occurrence line extended from the line approximate expression SD and the threshold value TH3 is the time at which the driver becomes drowsy. At this time, an actual drowsiness occurrence time declared by the driver is substantially consistent with the time Tc.

In the above description, the face image capturing camera 2 and Step S51 (see FIG. 2) of the ECU 3 constitute face information acquisition means for acquiring face information of a driver. Steps S52, S53, and S56 (see FIG. 2) of the ECU 3 constitute eye open time variation calculation means for calculating variation in the eye open time of the driver on the basis of the face information of the driver. Steps S54, S55, and S57 constitute face direction variation calculation means for calculating variation in the face direction of the driver on the basis of the face information of the driver. Step S58 constitutes vigilance assessment means for assessing the vigilance of the driver on the basis of the variation in the eye open time of the driver and the variation in the face direction of the driver.

Step S59 constitutes drowsiness occurrence assessment means for assessing whether or not there is the possibility of the occurrence of drowsiness in the driver on the basis of the increase/decrease tendency of the variation in the eye open time of the driver after the absentminded state of the driver has been detected from the vigilance of the driver assessed by the vigilance assessment means. Step S60 constitutes drowsiness occurrence time prediction means for predicting the time at which drowsiness occurs in the driver on the basis of a slope of an approximate expression obtained by approximating the variation in the eye open time of the driver and a threshold value set in advance when the drowsiness occurrence assessment means assesses that there is the possibility of the occurrence of drowsiness in the driver.

As described above, in this embodiment, the eye open time and the face direction left/right angle of the driver are detected on the basis of face image data of the face image capturing camera 2, the eye open time variation and the face direction left/right angle variation of the driver are calculated, and threshold processing is performed on the eye open time variation and the face direction left/right angle variation to detect the absentminded state of the driver, thereby accurately assessing the absentminded state which is not easily assessed. Therefore, the driver is reminded of the absentminded state before drowsiness occurs, thereby drawing the driver's attention.

Since the presence/absence of the transition from the absentminded state to the drowsiness occurrence state is assessed on the basis of the eye open time variation and the face direction left/right angle variation of the driver, when it is assessed that there is the possibility of the occurrence of drowsiness in the driver in the future, it is possible to give the driver a countermeasure (for example, chewing or the like) for suppressing drowsiness in the driver.

When it is assessed that there is the possibility of the occurrence of drowsiness in the driver in the future, since the expected drowsiness occurrence time of the driver is estimated, the time until drowsiness occurs is informed to the driver, thereby providing reference information (for example, the selection of parking to take shelter) as a countermeasure to get rest.

INDUSTRIAL APPLICABILITY

The invention provides a biological body state assessment device capable of accurately assessing the absentminded state of the driver.

REFERENCE SIGNS LIST

1: biological body state assessment device,
2: face image capturing camera (face information acquisition means),
3: ECU (face information acquisition means, eye open time variation calculation means, face direction variation calculation means, vigilance assessment means, drowsiness occurrence assessment means, drowsiness occurrence time prediction means).

The invention claimed is:
1. A biological body state assessment device comprising:
face information acquisition means for acquiring face information of a driver;
eye open time variation calculation means for calculating variation in an eye open time of the driver based on the face information of the driver;
face direction variation calculation means for calculating variation in a face direction of the driver based on the face information of the driver;
vigilance assessment means for assessing vigilance of the driver based on the variation in the eye open time of the driver and the variation in the face direction of the driver; and
drowsiness occurrence assessment means for assessing a possibility of drowsiness occurring in the driver based on an increase or a decrease in the variation in the eye open time of the driver after an absentminded state of the driver has been detected from the vigilance of the driver assessed by the vigilance assessment means, wherein the variation in the eye open time is a standard deviation of the eye open time or a dispersion of the eye open time, and wherein the variation in the face direction is a standard deviation of the face direction or a dispersion of the face direction.

2. The biological body state assessment device according to claim 1, wherein the vigilance assessment means assesses that, as the variation in the face direction of the driver becomes smaller, the vigilance of the driver is lowered.

3. The biological body state assessment device according to claim 1, further comprising:

drowsiness occurrence time prediction means for predicting a time at which drowsiness occurs in the driver based on a slope of an approximate expression obtained by approximating the variation in the eye open time of the driver and a threshold value set in advance when the drowsiness occurrence assessment means assesses a possibility of drowsiness occurring in the driver.

4. A biological body state assessment method, comprising:
acquiring face information of a driver;
calculating variation in an eye open time of the driver based on the face information of the driver;
calculating variation in a face direction of the driver based on the face information of the driver;
assessing vigilance of the driver based on the variation in the eye open time of the driver and the variation in the face direction of the driver; and
assessing a possibility of drowsiness occurring in the driver based on an increase or a decrease in the variation in the eye open time of the driver after an absentminded state of the driver has been detected from the vigilance of the driver,
wherein the variation in the eye open time is a standard deviation of the eye open time or a dispersion of the eye open time, and
wherein the variation in the face direction is a standard deviation of the face direction or a dispersion of the face direction.

5. The biological body state assessment method according to claim 4, wherein as the variation in the face direction of the driver becomes smaller, the vigilance of the driver is lowered.

6. The biological body state assessment method according to claim 4, further comprising:

predicting a time at which drowsiness occurs in the driver based on a slope of an approximate expression obtained by approximating the variation in the eye open time of the driver and a threshold value set in advance when a possibility of drowsiness occurring in the driver has been assessed.

* * * * *